United States Patent
Hawkins, III et al.

(10) Patent No.: US 10,500,440 B2
(45) Date of Patent: Dec. 10, 2019

(54) EXERCISE COMPUTER WITH ZOOM FUNCTION AND METHODS FOR DISPLAYING DATA USING AN EXERCISE COMPUTER

(71) Applicant: Wahoo Fitness LLC, Atlanta, GA (US)

(72) Inventors: Harold M. Hawkins, III, Atlanta, GA (US); Benjamin P. Johnston, Queensland (AU); Shane A. Byler, Mableton, GA (US)

(73) Assignee: Wahoo Fitness LLC, Atlanta, GA (US)

( * ) Notice: Subject to any disclaimer, the term of this patent is extended or adjusted under 35 U.S.C. 154(b) by 261 days.

(21) Appl. No.: 15/416,242

(22) Filed: Jan. 26, 2017

(65) Prior Publication Data

US 2017/0212666 A1    Jul. 27, 2017

Related U.S. Application Data

(60) Provisional application No. 62/287,328, filed on Jan. 26, 2016.

(51) Int. Cl.

| | |
|---|---|
| *G06F 3/14* | (2006.01) |
| *A63B 24/00* | (2006.01) |
| *G06F 17/21* | (2006.01) |
| *G06F 17/24* | (2006.01) |
| *G06F 3/0481* | (2013.01) |
| *G06F 3/0484* | (2013.01) |
| *A61B 5/00* | (2006.01) |
| *A61B 5/024* | (2006.01) |
| *A61B 5/11* | (2006.01) |

(52) U.S. Cl.
CPC ........ *A63B 24/0062* (2013.01); *G06F 3/0481* (2013.01); *G06F 3/04847* (2013.01); *G06F 17/212* (2013.01); *G06F 17/245* (2013.01); *A61B 5/02438* (2013.01); *A61B 5/11* (2013.01); *A61B 5/742* (2013.01); *A61B 2503/10* (2013.01); *G06F 2203/04803* (2013.01); *G06F 2203/04806* (2013.01)

(58) Field of Classification Search
CPC ..................................... G06F 3/14; G06F 3/17
USPC .................. 715/256, 800; 348/468; 707/741; 358/1.1
See application file for complete search history.

(56) References Cited

U.S. PATENT DOCUMENTS

| | | | | |
|---|---|---|---|---|
| 6,046,818 | A | * | 4/2000 | Benson ................. G06F 17/217 358/1.1 |
| 2008/0129865 | A1 | * | 6/2008 | Leonard ............... G11B 27/034 348/468 |
| 2012/0096005 | A1 | * | 4/2012 | O'Connor .............. G16H 10/20 707/741 |

(Continued)

*Primary Examiner* — Ruay Ho
(74) *Attorney, Agent, or Firm* — Polsinelli PC

(57) ABSTRACT

An exercise computer includes a page object that includes an ordered list of data fields. The ordered list includes a first data field pertaining to a first data value and a second data field pertaining to a second data value. A first layout stored defines a first cell having a position and size and a second cell, the cells for displaying the first data value and the second data value, respectively. A second layout defines a third cell also for displaying the first data value, but having a size and/or position different than those of the first cell. A processing unit of the exercise computer is configured to selectively display the first layout and the second layout and to populate each of the cells with the corresponding data value.

24 Claims, 10 Drawing Sheets

(56) References Cited

U.S. PATENT DOCUMENTS

2012/0240038 A1\* 9/2012 Curtis .................. G06F 17/243
715/256

\* cited by examiner

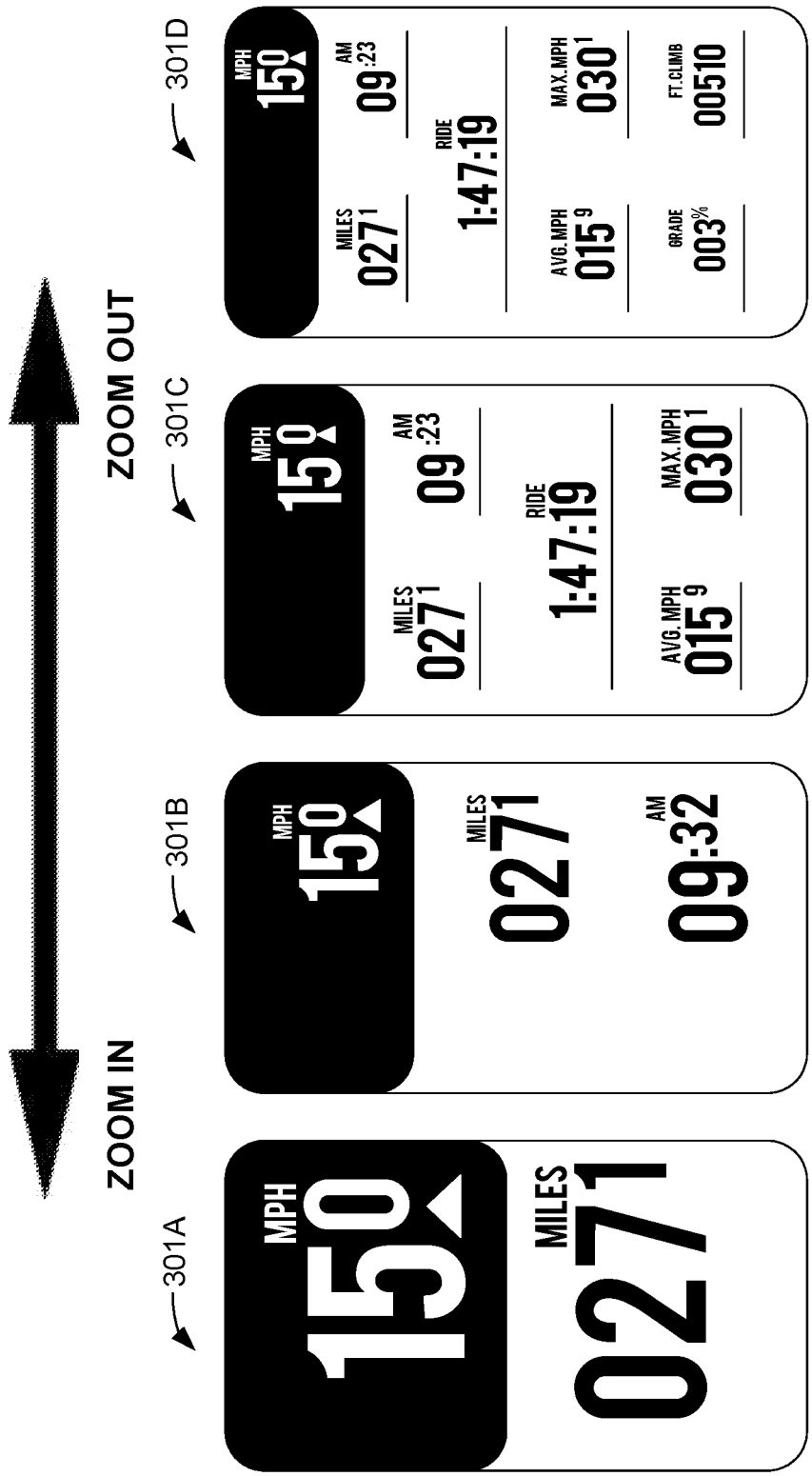

EXERCISE COMPUTER WITH ZOOM FUNCTION AND METHODS FOR DISPLAYING DATA USING AN EXERCISE COMPUTER

CROSS-REFERENCE TO RELATED APPLICATION

This application is related to and claims priority under 35 U.S.C. § 119(e) from U.S. Patent Application No. 62/287,328, filed Jan. 26, 2016, titled "EXERCISE COMPUTER WITH ZOOM FUNCTION," the entire contents of which are incorporated herein by reference for all purposes.

TECHNICAL FIELD

Aspects of the present application involve cycling and other exercise computers, and more particularly a display zoom functionality for such computers.

BACKGROUND

A cycling computer is a device intended to be worn by a rider or more typically mounted on a bicycle, such as on the handlebars or stem. The cycling computer monitors and displays information such as speed, ride distance, time, location, maps, power, cadence and others. Conventionally, cycling computers have a series of pre-set "pages" to display some arrangement of data. Each page contains a fixed number of cells, and each cell contains one or more data items, such as speed, distance, heart rate, time, etc. Changing the layout of the page or the data items in each cell is typically a pre- or post-workout activity, because doing so requires significant interaction with the cycling computer by the user, which is inconvenient and unsafe to do while moving. Furthermore, since the display of a cycling computer is fixed, selecting a layout involves a tradeoff between large text for readability and quantity of data because more data fields requires smaller cells, and hence smaller text.

It is with these observations in mind, among others, that various aspects of the present patent were conceived and developed.

SUMMARY

Implementations described and claimed herein address the foregoing problems, among others, by providing systems and methods for displaying exercise data using an exercise computer. In one implementation, an exercise computer is provided. The exercise computer includes a processing unit in communication with a non-transitory storage and a display. The non-transitory storage includes a page object that includes an ordered list of data fields. The ordered list includes a first data field pertaining to a first data value and a second data field pertaining to a second data value. The non-transitory storage further includes a first layout stored in the non-transitory storage that defines a first cell having a position and size and a second cell, the cells for displaying the first data value and the second data value, respectively. The non-transitory storage also includes a second layout stored in the non-transitory storage that defines a third cell also for displaying the first data value, but having a size and/or position different than those of the first cell. The processing unit is configured to selectively display the first layout and the second layout and to populate each of the first cell, the second cell, and the third cell with the first data value, the second data value, and the first data value, respectively.

In another implementation, a method of displaying exercise data using an exercise computer is provided, the exercise computer including a processing unit coupled to a non-transitory storage and a display. The method includes retrieving a page object from the non-transitory storage that includes an ordered list of one or more data fields, each of the data fields pertaining to a respective data value. The method further includes retrieving a first layout from the non-transitory storage that defines first cells for displaying a first set of the data values and displaying the first layout populated with the first set of the data values. In response to receiving a zoom level change command, a second layout is retrieved, the second layout defining second cells for displaying a second set of the data values different from the first set of data values on the display. The method also includes displaying the second layout populated with the second set of the data values.

In another implementation, a non-transitory tangible computer-readable storage media storing computer-executable instructions for performing a computer process on an exercise computer including a processing unit in communication with one or more memory devices and a display is provided. The computer process includes retrieving a page object from the non-transitory storage that includes an ordered list of one or more data fields, each of the data fields pertaining to a respective data value. The process further includes retrieving a first layout from the non-transitory storage that defines first cells for displaying a first set of the data values and displaying the first layout populated with the first set of the data values. In response to receiving a zoom level change command, a second layout is retrieved, the second layout defining second cells for displaying a second set of the data values different from the first set of data values on the display. The process also includes displaying the second layout populated with the second set of the data values.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF DRAWINGS

The foregoing and other objects, features, and advantages of the present disclosure set forth herein will be apparent from the following description of particular embodiments of those inventive concepts, as illustrated in the accompanying drawings. It should be noted that the drawings are not necessarily to scale; however the emphasis instead is being placed on illustrating the principles of the inventive concepts. Also, in the drawings the like reference characters may refer to the same parts or similar throughout the different views. It is intended that the embodiments and figures disclosed herein are to be considered illustrative rather than limiting.

FIGS. 3A-D are example screenshots illustrating a progression of zoom levels for displaying data values of a page object;

DETAILED DESCRIPTION

Figure 1:
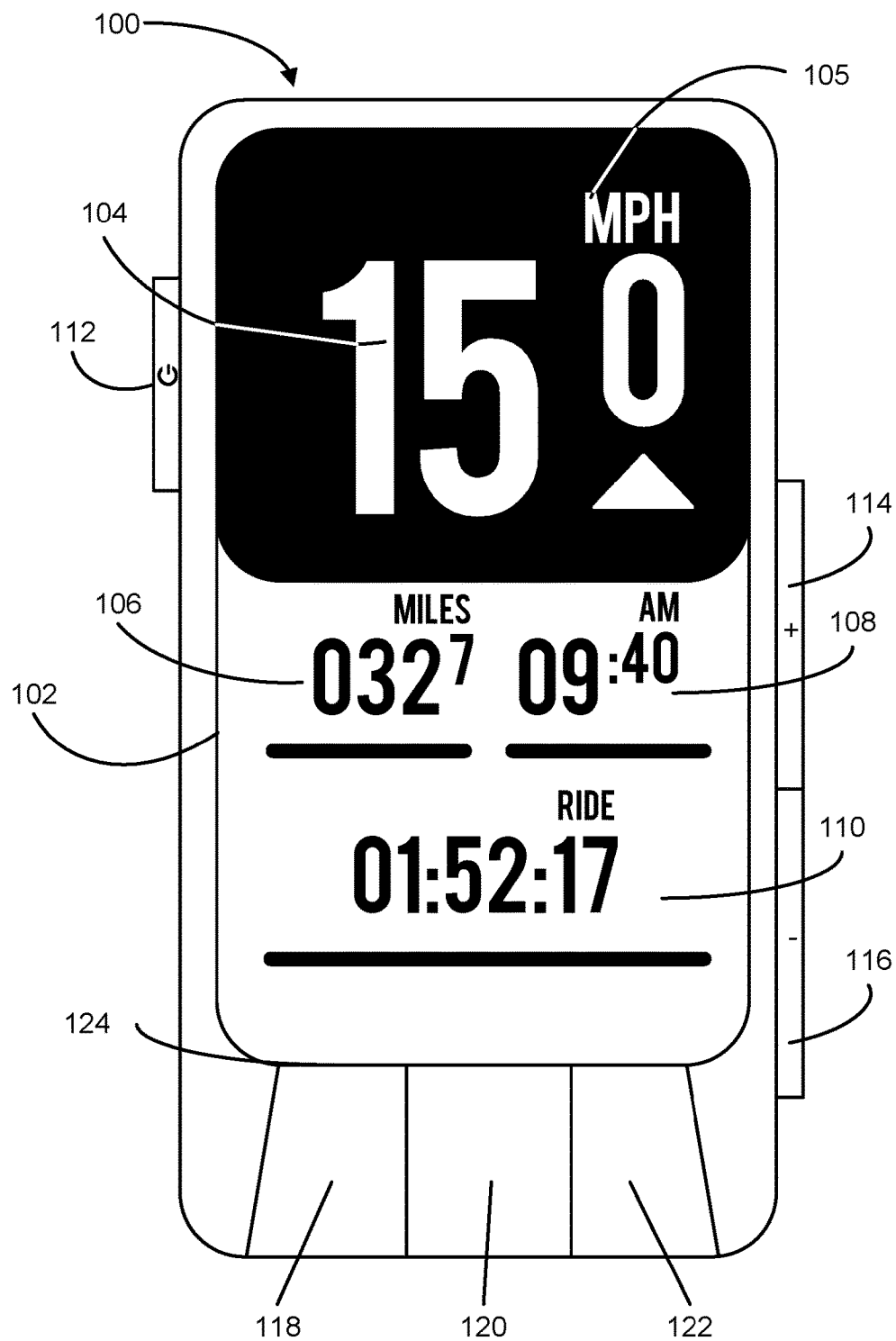
FIG. 1 is a front view of an exercise computer in accordance with an embodiment of the present disclosure.

Aspects of the present disclosure provide an exercise computer, such as a cycling computer, or other mobile computing device with a relatively small display screen, with a convenient and efficient way to organize data fields and to interact with the exercise computer to zoom in and out to display fewer but larger sized data values or greater but smaller sized data values. In one possible implementation, the system provides a mechanism whereby a user can define a page with some number of data fields that are prioritized according to user preferences. In one example, the page is an ordered list of data fields. The exercise computer provides an interface, such as dedicated hardware buttons, that allows a user to zoom in or out of the page. Zooming in or out displays fewer but relatively larger fields and less but relatively smaller fields, respectively. In one possible implementation, the page is initially displayed with all of the defined data fields in locations based on priority or as customized by the user and each value associated with the data fields is at a size sufficient to fit within the confines of the display. As the user zooms in, for each zoom selection, some lesser number of data fields is displayed in progressively larger size based on priority of the data fields. The data fields are displayed on the same page, but the zoom selection is used to determine which subset of the data fields to render on the page, ranging from one to all data fields, based on priority. So, for example, for a page having three data fields, all three data fields are displayed at the lowest zoom level, with each occupying about ⅓ of the display space. Note, as discussed in more detail herein, the display spacing is not necessarily evenly divided. When the user presses a zoom up button, the exercise computer may then reference a display configuration for the next zoom level for the same page. Based on a prioritized data field list, only the first and second ranked display fields may be rendered on the display with each occupying about ½ of the display space. If the cyclist subsequently zooms out, for example by pressing an appropriate button, the three data fields will again be displayed. Alternatively, if the cyclist subsequently zooms in, the highest priority data field will occupy all of the display space by using a rendering configuration for the same page that causes only one field to be displayed.

During the majority of a ride, a cyclist might want a couple of big numbers on the screen that are easy to see at a glance, such as speed and distance travelled. However, for parts of the ride, the cyclist may want to see other data fields, such as their cadence, their average speed or their maximum heart rate. To preserve readability, in a conventional bike computer, such specific fields may be set up on one or more separate pages that the cyclist scrolls to from the main page since the specific fields are desired too infrequently to deserve precious screen real estate. Putting these on a separate page means there are more pages cluttering the navigation, and viewing these pages means the cyclist loses their key data on the original page.

Exercise computers according to the present disclosure generally include one or more page objects, each having an ordered list of data fields and a current zoom level. The ordered list of data fields provides a ranking or priority of data fields. At runtime, an exercise application or similar software executed by the exercise computer retrieves the current page object, its current zoom level and a layout corresponding to the current zoom level. Each layout includes cells that correspond to the different priority levels of the page object. Accordingly, the layout is drawn on a display of the exercise computer and the cells are populated with the data values corresponding to the data fields of the page object based on their priority. As the user changes zoom levels, such as by pressing a zoom-in or zoom-out button, a new layout corresponding to the new zoom level is retrieved, drawn, and populated accordingly. Similarly if the user changes pages in embodiments in which the exercise computer stores multiple pages, the exercise app retrieves the new page object, its current zoom level, and the corresponding layout and proceeds to draw and populate the layout.

In certain embodiments, the exercise computer can be communicatively coupled with a remote computing device, such as a laptop or smartphone, on which a companion application is executed. The companion application enables various functions including customization of the page objects. For example, in certain implementations, the companion application allows a user to change the data fields to be displayed and the priorities of those data fields. In response to such changes, the companion application sends an update message that causes the exercise computer to update the stored page objects accordingly.

Conventionally, a page in a cycling computer is organized around a group of similar data relevant to a specific content or scope. For example, a conventional cycling computer may have a page with data fields relevant to climbing (e.g., speed, slope, power), a page with data fields relevant to overall workout (e.g., total time, total miles, average speed), and the like. Changing pages thus changes the overall concept of the page. In contrast, the zoom features discussed herein may be implemented in any given exercise device, whether cycling computer or otherwise, that include pages to further enable zooming into specific fields of interest within a particular page. Accordingly, besides providing a variety of page layouts, aspects of the present disclosure provide more than one display layout for any given page, where the display layouts conform to zoom levels linked to the prioritized list of data fields for any page. Thus, a user may change between pages and may also change between zoom levels for any given page and zoom into some particular data fields or fields for any given page.

FIG. 1 is a front view of an exercise computer 100 (also referred to herein as a cycling computer 100) in accordance with one embodiment of the present disclosure. FIG. 1 illustrates a front view of the exercise computer 100, which includes a display 102, and various data display elements displaying data values and corresponding description fields for typical data fields interesting to a cyclist. The data fields shown in FIG. 1 include a speed data field 104 for displaying the user's current speed, a distance data field 106 for displaying the total distance travelled, a time of day data field 108, and a total ride time data field 110. In certain implementations, the units of measure and other parameters of the data fields can be modified according to user preferences. For example, the speed data field 104 may be toggled between speed in miles per hour (MPH) and kilometers per hour (KPH). Similarly, the distance data field 106 can be changed from miles to kilometers and the time of day data field 108 can be changed from a 12-hour (which indicates a.m. and p.m.) to a 24-hour display. The illustrated exercise computer 100 further includes a power button 112 to turn the exercise computer 100 on and off and two zoom buttons (a zoom-in button 114 and a zoom-out button 116).

In the embodiment of FIG. 1, the exercise computer 100 has a generally rectangular shape with the long sides of the rectangle being on the left and right sides of the exercise computer 100, and the short sides of the rectangle being along the top and bottom of the exercise computer 100. Other shapes and orientations are possible, and it is also possible to provide the exercise computer 100 with a gyroscope, an accelerometer, or similar sensor, such that if it is mounted as shown in FIG. 1 the display will be vertical but if it is mounted in a position that is rotated 90 degrees relative to that shown in FIG. 1, then the display automatically adjusts to a horizontal orientation in which the data fields are along the longer axis. In such an alternative, there may be alternative sets of zoom renderings for vertical or horizontal placement.

In the embodiment of FIG. 1, the zoom-in button 114 and the zoom-out button 116 are arranged adjacent to each other, i.e., on the same side of the exercise computer 100, and the power button 112 is position opposite the zoom-in button 114 and the zoom-out button. In this way, a user may grasp the exercise computer 100 with fingers on both sides of the exercise computer 100 and provide locations for the finger or thumb opposing the intended button to use the opposing sidewall to squeeze the exercise computer 100 without inadvertently depressing an unintended button. For example, if a user uses the index finger of her right hand to depress either the zoom-in button 114 or the zoom-out button 116, there is space below the power button 112 for the user to place her thumb and momentarily grasp the exercise computer 100 to depress the zoom-in button 114.

In certain implementations, the exercise computer 100 includes additional buttons, to perform additional functions of the exercise computer 100. In the embodiment of FIG. 1, for example, the exercise computer includes a page button 118, a start button 120, and a stop button 122 located along the bottom edge of the exercise computer 100 adjacent a bottom edge 124 of the display 102. The additional buttons shown in FIG. 1 are examples of additional buttons and button configurations that may be implemented in embodiments of the present disclosure. In other implementations, that additional buttons may include, without limitation, a pause button, a page-forward or page-back button, a reset button, a lap button, and other buttons to perform common exercise computer functions. In certain implementations, one or more of the additional buttons may be a multi-function button. For example, the start button 120 and the stop button 122 may be combined into a multi-function button that starts or stops the device based on the state of the device (e.g., when the clock or routine is started, the following depression of the button will execute a stop). In another example, the same button may initially start, and pause, and stop; or start, pause and restart, and a separate button is used to stop.

Figure 2:
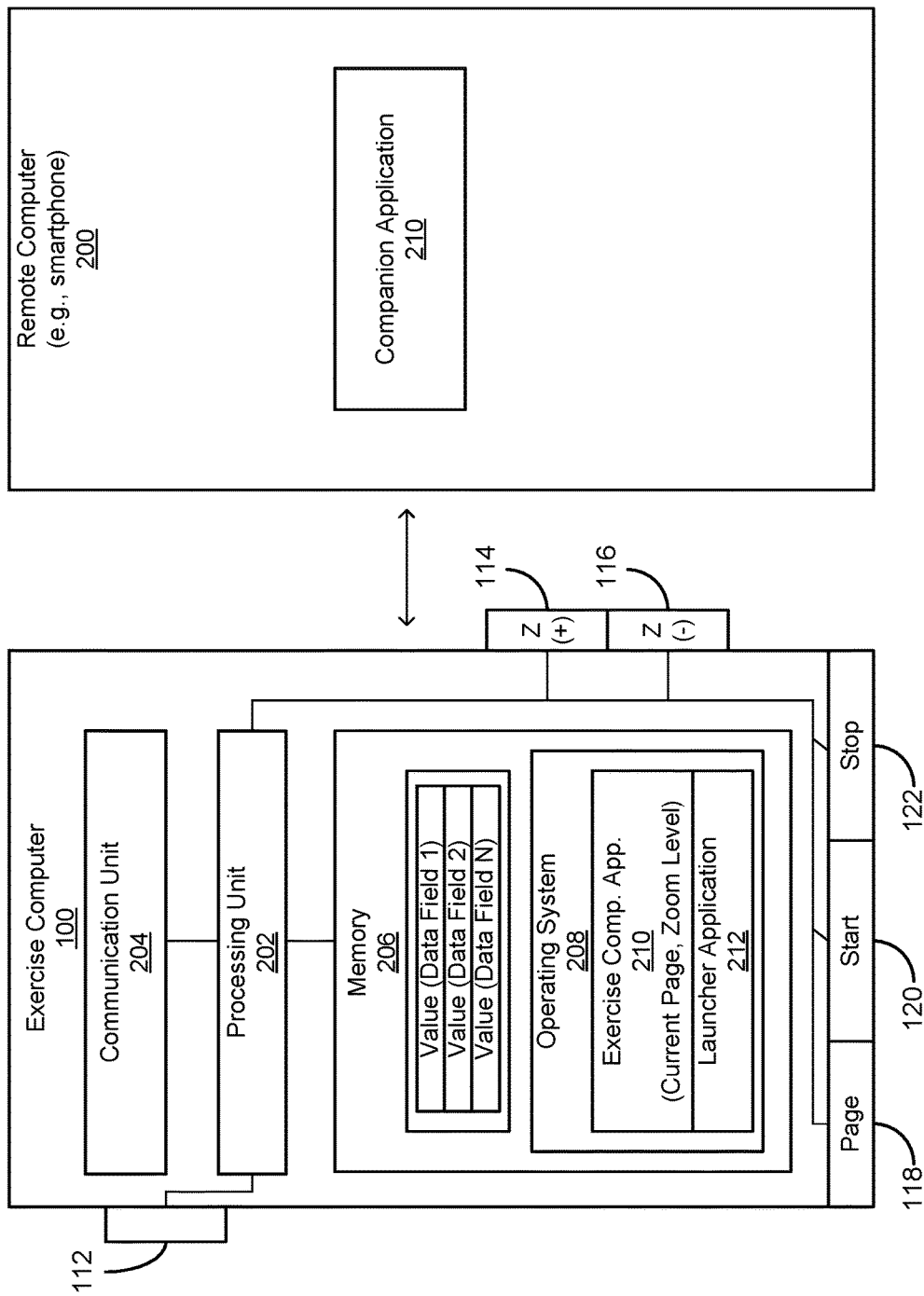
FIG. 2 is a schematic illustration of the exercise computer of FIG. 1 in communication with a remote computing device.

FIG. 2 is a diagram illustrating hardware, firmware, and software components of the exercise computer 100 as well as a remote computing device 200 that may be used to configure attributes of the exercise computer 100. In some instances, the exercise computer 100 is referred to herein as a computer 100 and the remote computer 200 is referred to as a smart phone 200. It is should be recognized, however, that a cycling computer is but one specific type of device that may benefit and use the zoom features discussed herein and other devices may take advantage of the features discussed herein. Similarly, the remote computer 200 may be referred to as a smart phone but laptop computers, desktop computers, tablets and other devices may similarly be used to perform the functions associated with the remote computer 200. In one specific embodiment, the remote computer 200 is a mobile computing device, such as a smart phone or tablet, running an operating system 208, such as a version of iOS™ or Android™. In one specific embodiment, the hardware platform for the exercise computer 100 is an Android™-based device containing a processing unit 202, a communication unit 204 (for sending and receiving data through a wired connection and/or a wireless connection such as one or more of Wi-Fi, global positioning system (GPS), and Bluetooth®), a memory 206, and a set of buttons that are used to initiate various functions managed by an application, such as a fitness application, running on the exercise computer 100 and displayed to a user by a display 102 (shown in FIG. 1). As discussed in the context of FIG. 1, the set of buttons of the exercise computer 100 includes a power button 112, a zoom-in button 114, a zoom-out button 116, a page button 118, a start button 120, and a stop button 122. The various buttons of the exercise computer 100 provide a user with a mechanism to interact with the processing unit 202 and cause various actions to occur. It is possible that input/output (I/O) hardware may provide an interface between the buttons and the processing unit. The operating system 208, in an example, is also Android based and provides various functionalities including a file system, a location service, Wi-Fi or other communications management, and low level Bluetooth® management.

The smart phone 200 may include a companion application 210 (or companion "app") configured to interact with the exercise computer 100 and the application running thereon. In various embodiments, the companion app 210 and the smart phone 200 may communicate with the exercise computer 100 using a wired connection or any of various possible wireless communication mechanisms such as Bluetooth®, Bluetooth® Low Energy, and WiFi.

The processing unit 202 of the exercise computer 100 is in communication with the memory 206, which includes computer executable instructions for running various programs to obtain and display data, as well as other functions. For example, the memory 206 includes an exercise computer application 210 (or "exercise computer app") for performing various functions associated with the exercise computer 100 and for providing a user interface and a launcher application 212 for launching the exercise computer app 210 on startup of the exercise computer 100. The exercise computer 100 may also include geographic positioning system (GPS) chip sets to track and/or compute location, distance, speed and other information. The memory 206 may also store data for retrieval after an exercise session, such as a bike ride, and the computer may include various possible hardware devices to download that data through a wired (e.g., a port) or wireless connection (e.g., a radio providing Bluetooth® or Wifi).

Figure 3E:
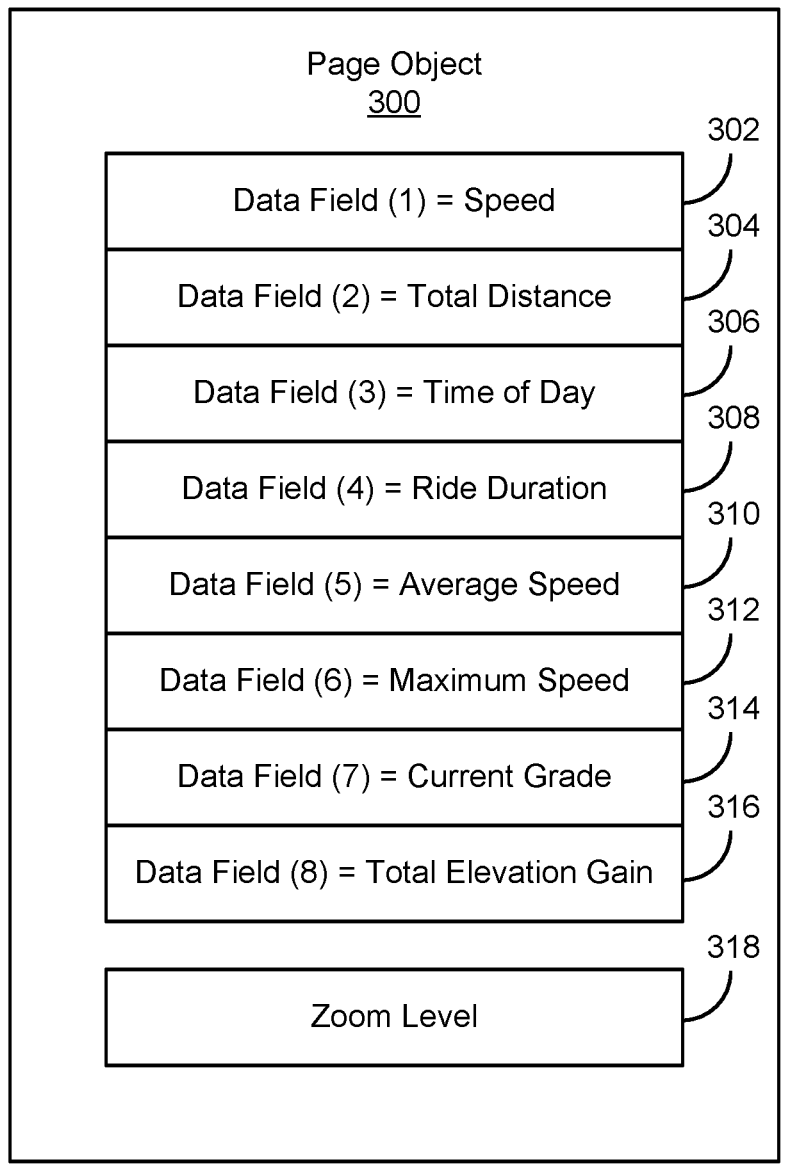
FIG. 3E is a schematic illustration of a the page object corresponding to the screenshots of FIGS. 3A-D.

Referring now to FIGS. 3A-3E, FIGS. 3A-3D are example screenshots 301A-D illustrating four levels of zoom of a page object 300 shown in FIG. 3E. The page object 300 includes eight (8) total data fields 302-316. One or more page objects, such as the page object 300, are stored in memory, such as the memory 206 of the exercise computer 100 shown in FIGS. 1 and 2. As shown in FIG. 3E, the data fields 302-316 of the page object 300 are assigned a priority. In the specific example of FIGS. 3A-3E, the "Speed" data field 302 is assigned the highest priority ("1") while the "Total Elevation Gain" data field 316 is assigned the lowest priority ("8"). Accordingly, in this example and based on the prioritized list of the page object 300, from lowest priority to highest, the data fields are a total elevation data field 316 (e.g., the total number of feet climbed during the current ride), a grade data field 314 (e.g., the grade as a percentage grade of whatever surface the cyclist is on), a maximum speed data field 312, an average speed data field 310, a ride time/duration data field 308, a current time data field 306, a total distance data field 304, and a current speed data field 302. The page object 300 further stores a zoom level 318 corresponding to the current zoom level associated with the page object 300. The data fields 302-316 of the page object 300 may be realized with a unique key to a data store, database, or other memory structure implemented in the exercise computer, where the unique key is to a particular data value for a data field. The data value may also be associated with other information for the value.

Data values stored in each of the data fields 302-316 may be obtained through various sensors and components in communication with the exercise computer 100. For example, total elevation gain, current grade, and maximum and average speeds can be obtained using a GPS unit or similar geolocation device included in or in communication with the exercise computer. Other sensors and components, such as a cadence sensor, a wheel-mounted speed sensor, an accelerometer, an altimeter, a heart rate monitor, and a clock may further be included in or in communication with the exercise device to provide data values for the various data fields or data from which such data values may be calculated. Such sensors and components may be integrated into the exercise component or in communication with the exercise computer, such as by a direct wired connection or a wireless connection. For example, in certain embodiments, the exercise computer receives GPS data and/or accelerometer data from a smart phone of the user. Accordingly, data values may be stored in memory based on computation from the processing unit, may be obtained from a separate device (e.g., a heartrate monitor, a remote computing device), or may be computed and stored in memory in other ways.

The priority assigned to each data element 302-316 may be represented in various ways. For example, in certain embodiments, the data fields 302-316 are stored as an array in which an array index also indicates priority. In other embodiments, the data fields are stored as a table with each row including a data value for the data field and a priority value and, in certain embodiments, additional details corresponding to the data field, such as the units of measure to display.

FIGS. 3A-3D illustrate the page object 300 as rendered by an exercise computer, such as the exercise computer 100 shown in FIGS. 1 and 2, and presented on a display 102 of the exercise computer 100. FIG. 3D illustrates a fully zoomed out view of the page object 300 such that data values corresponding to each of the data fields 302 are shown on the display 102. In certain implementations, one or more of the data values may be highlighted or otherwise presented differently for emphasis. For example, in each of the zoom levels depicted in FIGS. 3A-3D, speed is presented as white text on a black background while the other data values are presented as black text on a white background. In certain implementations, the highest priority data field is highlighted at each zoom level. Alternatively, the user may select one or more data fields to highlight at one or more zoom levels.

As shown in FIGS. 3A-3D, various units of measurement or other information are shown when the data values are rendered for display. For example, the display indicates that speed is displayed in miles per hour ("MPH") and elevation gain in feet of climb ("FT. CLIMB"). In certain embodiments, the user may configure the data fields to show alternate units of measure or to display certain data fields in alternate formats. For example, speed values may be shown in kilometers per hour ("KPH") instead of miles per hour and elevation gain may be shown in meters ("M GAIN") as opposed to feet. As another example, the current time may be changed from a 12-hour time format to a 24-hour time format. Accordingly, each data field may further be associated with one or more text fields or information attributes that are stored with the data the value and linked to the data field. Thus, for example, when the data field in a page is total distance, the total distance data field includes a key or other reference to a memory location where the data value for total distance (e.g., 27.1) and the information attribute (e.g., miles), is stored. The exercise computer then renders the data value in accordance with the information attribute.

As shown in the progression from FIGS. 3A to 3D, when a user zooms out, such as by depressing the zoom-out button 116 (shown in FIGS. 1 and 2), more data fields of the page object 300 are shown on the display but in a smaller format. Similarly, when a user zooms in, such as by depressing the zoom-in button 114 (also shown in FIGS. 1 and 2), fewer data fields of the page object 300 are shown on the display but in a larger format. The location and size of the value and information for any data fields to be displayed at a given zoom level are provided in a display layout for the zoom level. Thus, viewing from FIG. 3D to FIG. 3A, as the user depresses the zoom-in button, six of the eight total data fields are displayed (as shown in FIG. 3C), three of the eight total data fields are displayed (as shown in FIG. 3B), and two of the eight total data fields are displayed (as shown in FIG. 3A). Accordingly, whenever the exercise computer is active and displaying data, the user can use the zoom buttons to quickly see more data fields or fewer data field value by zooming in and out. Notably, as the user zooms out (as shown by the progression from FIG. 3A to 3D) the data fields presented at previous zoom levels remain visible. For example, both speed and distance are visible at each zoom level. So, when zooming out, additional data fields of the page are revealed in each successive zoom out until all fields are displayed.

As previously discussed, exercise computers in accordance with this disclosure store one or more page objects, each of which includes an ordered list of data fields. The ordered list of data fields generally corresponds to data values available for display by the exercise computer such that the order of the list generally corresponds to the relative priority or rank of particular data fields. Accordingly, as a user moves between zoom levels, more or fewer data fields are displayed by the exercise computer based on their relative priority.

Exercise computers in accordance with the present disclosure can store multiple page objects, each having a different ordered list of data fields. The number and type of data fields of the ordered lists maintained in an exercise computer can vary. Accordingly, any two page objects for a given exercise computer may include ordered lists that differ in one or more of the data fields included, the quantity of data fields included, the order of the data fields, and the like.

Figure 4:
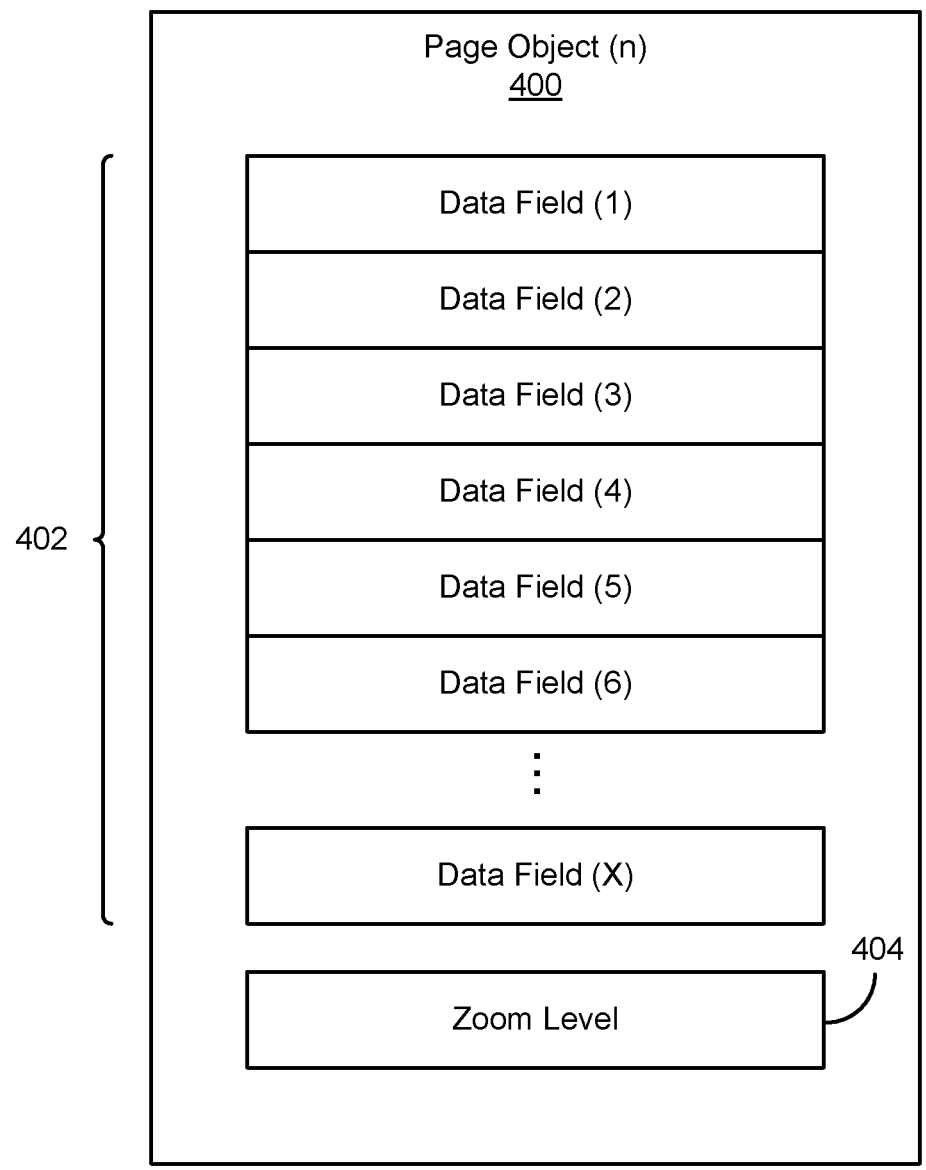
FIG. 4 is a schematic illustration of a page object in accordance with the present disclosure.

FIG. 4 illustrates a generic page object 400, with an ordered list 402 of data fields. Page object 400 is page object n of a set of page objects stored in an exercise computer, where n is any suitable number of page objects. Similarly, the ordered list 402 includes up data fields (1) to (X), where (X) represents any suitable number of data fields. The page object 400 further includes a zoom level 404 corresponding to the current zoom level for the page object 400. The zoom level 404 may be stored such that the most recent zoom level for the page object 400 is used when the page object 400 is loaded and rendered by the exercise computer such as when the exercise computer is turned on or the user cycles between different pages.

Figures 5A, 5B:
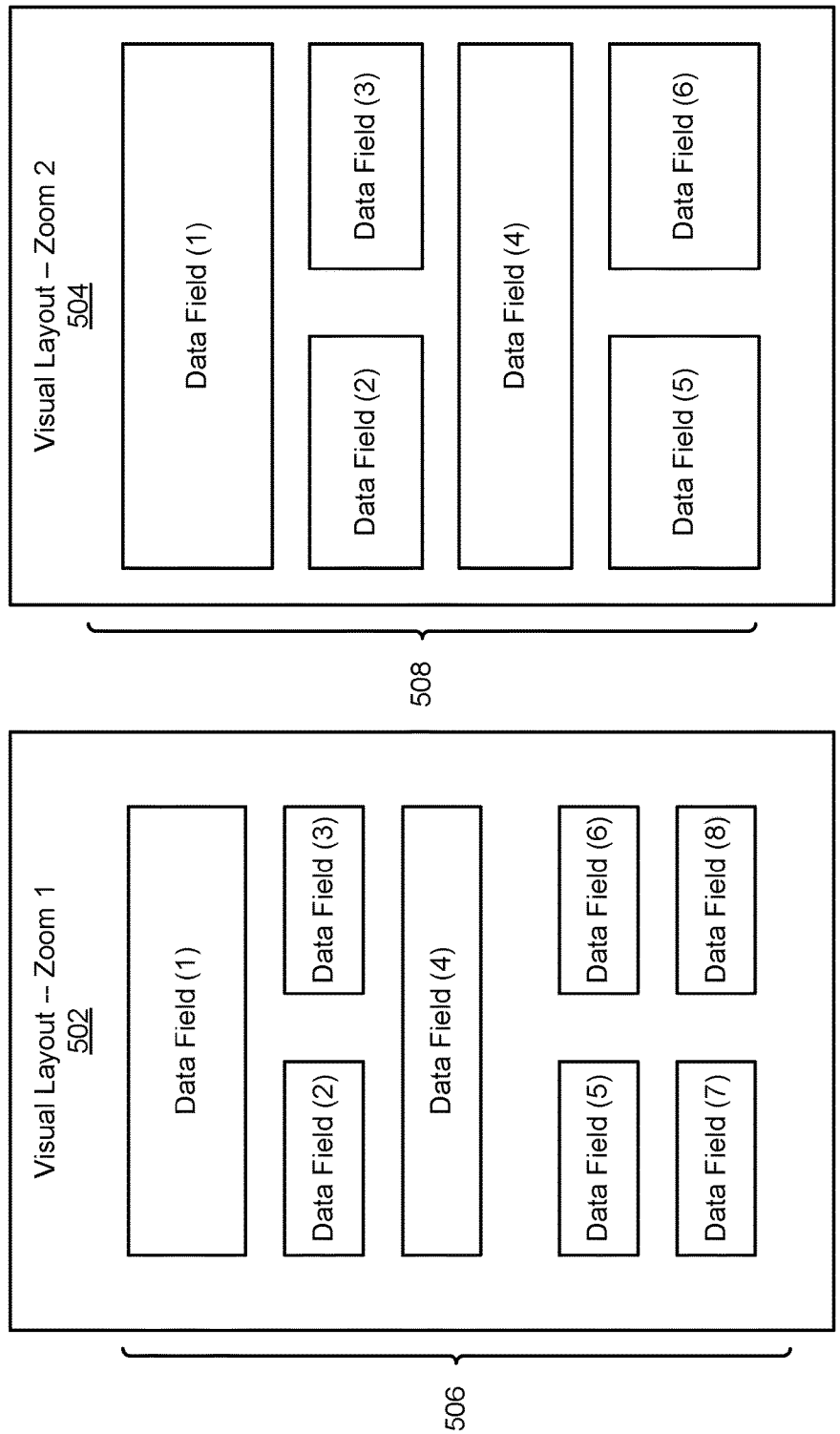
FIGS. 5A-B are schematic illustrations of layouts for displaying data values of a page object.

The exercise computer further includes multiple layouts for use in rendering page objects, such as the page object 400 shown in FIG. 4. For example, FIGS. 5A and 5B are schematic illustrations of a first layout 502 and a second layout 504, respectively. Each zoom level available has a corresponding layout. For example, the first layout 502 is at a first zoom level ("Zoom 1") and the second layout 504 is at a second zoom level ("Zoom 2"). Each layout further includes one or more cells defined by a coordinate (such as an X,Y coordinate relative to the exercise computer display) and a size. As shown in FIG. 5A, the first layout 502 includes cells 506 for Data Field (1) through Data Field (8). In contrast and as shown in FIG. 5B, the second layout 504, which is zoomed in relative to the first layout, includes cells 508 corresponding only to Data Field (1) through Data Field (6), but each of the cells 508 corresponding to Data Field (1) through Data Field (6) are rendered larger relative to the data fields of the first layout 502.

During rendering, the exercise app selects the layout corresponding to the current zoom level and populates each of the cells with the data values corresponding to the data fields of the page object being rendered. To do so, each cell of a given layout is assigned a number or other value, such as 0-9, that corresponds to a rank or priority of a data field. In certain implementations, the cells are ordered from top to bottom and left to right although other orderings and arrangements are possible. The cells are then populated with the corresponding data field having the same priority or rank. For example, cell "0" will be populated with the contents of Data Field "0" of the current page object, cell "1" will be populated with the contents of Data Field "1" of the current page object, and so on.

In certain implementations, each data field is assigned a unique key or similar identifier that is used to look up or otherwise obtain the current value associated with the data field. The unique key or identifier is also used to obtain a corresponding name, title, or similar text corresponding to the data field (e.g., "MPH", "FT. GAIN", "% GRADE", etc.) to be displayed within the cell. So, for example, current speed is obtained and/or computed, and the value is stored in memory at a location corresponding to the unique key for the current speed data field. The title for the field, "MPH", is also located at the same memory location such that the exercise application can retrieve both the data value and title and subsequently draw both in the appropriate cell.

In certain implementations, the page objects of the exercise computer are fixed. However, in other implementations, the page objects can be customized by a user. For example, in certain embodiments, the user can create or delete page objects, reorder page objects, and change the ordered list of data fields for a given page object by one or more of adding, deleting, and reordering the data fields of the page object. Although an exercise computer may allow a user to customize page objects, the exercise computer may also include one or more default page objects and layouts to be used prior to customization by the user or in lieu of the user creating customized page objects or layouts altogether.

Figure 6:
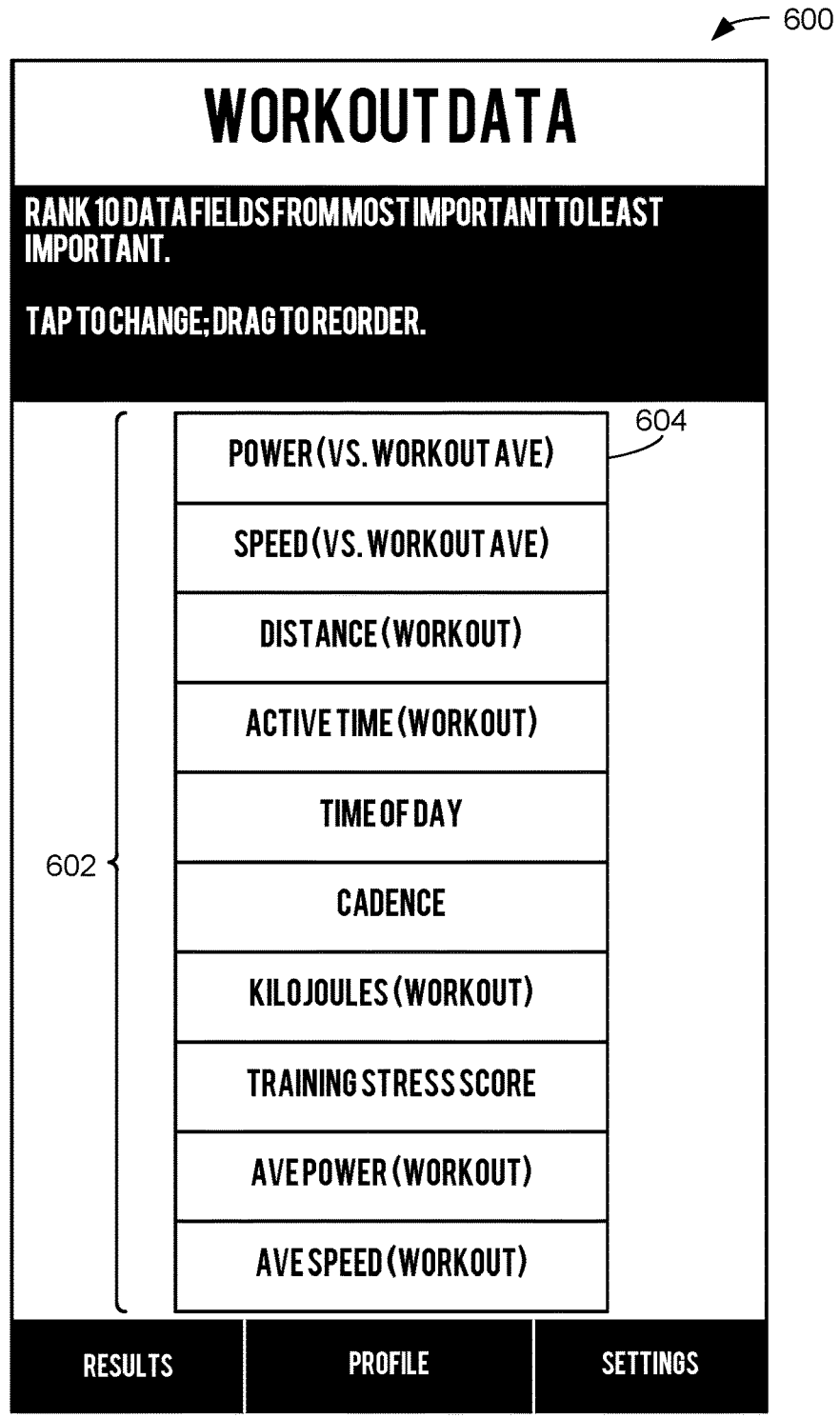
FIG. 6 is an example screenshot of a companion application for customizing page objects stored in an exercise computer.

In certain implementations, page objects of the exercise computer are customizable through a companion app running on either the exercise computer itself or a remote computing device in communication with the exercise computer. For example, FIG. 6 is an example screenshot 600 of a companion app that can be used to customize a page object of the exercise computer. In certain implementations, when the companion app connects, such as by way of Bluetooth® or other wired or wireless connection, the companion app downloads or otherwise obtains data from the exercise computer including, but not limited to the number of pages, the data field lists for each page, and any other data corresponding to the page objects and layouts of the exercise computer. The user is initially provided with a list of pages, and by selecting a page (e.g., by touching the page), the user is presented with a display of the details concerning the page such as shown in FIG. 6. The page information is displayed on the smart phone display as an interactive list 602 of data elements (such as data element 604) that the user may customize. For example, in certain implementations, the user can reorder the interactive list 602 of data fields by dragging the data fields to new positions within the list or can change a particular data field to a different data field type by tapping the data field and selecting a substitute data field from a list of available data fields. Changes to the list of data fields are sent as an update command to the exercise computer app over Bluetooth® (or other connection) and, in response, the exercise app updates the ordered list of the corresponding page object. If the updated page object corresponds to the currently loaded page, the exercise app may further redraw the current page to match the update page object. Alternatively, the exercise app may automatically load a page in response to receiving and executing an update command for the corresponding page object. This has the effect of showing the user's changes in real-time on the device. An updated ordered list is stored in the exercise computer app and used by the exercise app until the user further customizes the ordered list or reverts the exercise computer to factory settings.

As shown in FIG. 6, the companion app displays an ordered list 602 of data fields. In this example, the ordered list is presented with the highest priority data field as the first entry and the subsequent entries ranked based on their position in the ordered list. Accordingly, the second entry is the second priority data field. The data fields shown may correspond to those of an existing page object being edited by the user of the companion app or may correspond to a new ordered list for a new page object. Through the companion app, the user interacts with the ordered list 602 to set a preferred order of the data fields. For example, in certain implementations, the user is able to add, delete, and/or change the specific data fields included in the ordered list and the order of the data fields within the list by, for example, clicking, dragging, or otherwise providing input to the companion app. When finalized by the user, the ordered list is loaded into the exercise computer or used to modify an existing ordered list in the exercise computer, such as by wirelessly transmitting the ordered list to the exercise computer from the remote computing device.

In one specific embodiment, an exercise computer app, such as the exercise computer app 210 shown in FIG. 2, resides on the exercise computer and maintains the ordered lists data fields of page objects stored in the exercise computer. As previously discussed, each page object includes a current zoom level and an ordered list of data fields that are used to select and populate a corresponding layout, respectively. In implementations having multiple page objects, the exercise computer app enables the user to change pages. For example, the exercise computer 100 of FIGS. 1 and 2 includes a page button 118 that, when pressed, causes the exercise computer 100 to cycle through and display page objects stored in the exercise computer 100. The app and exercise may initially include a default list of pages each having a default list of data fields. In certain implementations, the default list of pages and data fields may be customized or otherwise modified by the user.

In certain implementations, the exercise computer app recognizes and pairs with external sensors, such as heart rate monitors, power meters, cadence sensors, speedometers, and the like. In one example, as such sensors pair to the exercise computer app, new data fields relevant to that sensor are automatically inserted into the default page lists. So, for example, if a page object has a default data field corresponding to a heart rate, pairing a hear rate sensor through the exercise computer app automatically adds the heart rate data field to the page object. In another example, the default page objects do not initially include data fields for data from externally connected devices but instead such data fields can be added by a user through the exercise computer app or the companion app. In one example, connection or detection of an externally connected device, such as a heart rate monitor, cadence sensor, or the like, may cause a data field to be added to the page object at some position within the ordered list of data fields of the page object. In certain instances, addition of the new data field may cause another field to be bumped off the ordered list of the corresponding page object. For example, if a page object includes ten data fields and a heart rate monitor is connected to the exercise computer, a heart rate data field may be automatically added to the third position of the ordered list and the remaining data fields shifted down accordingly, resulting in the previous tenth data field being bumped off the ordered list for the page object. Accordingly, if the current page object includes a heart rate data field, heart rate data will be displayed (assuming the current zoom level includes the heart rate data field). If the current page object does not include a heart rate data field in its ordered list, the heart rate data field is automatically added to the ordered list at a default position or a position chosen by the user when the heart rate monitor is paired to the exercise computer and the other data fields are rearranged accordingly.

Figure 7:
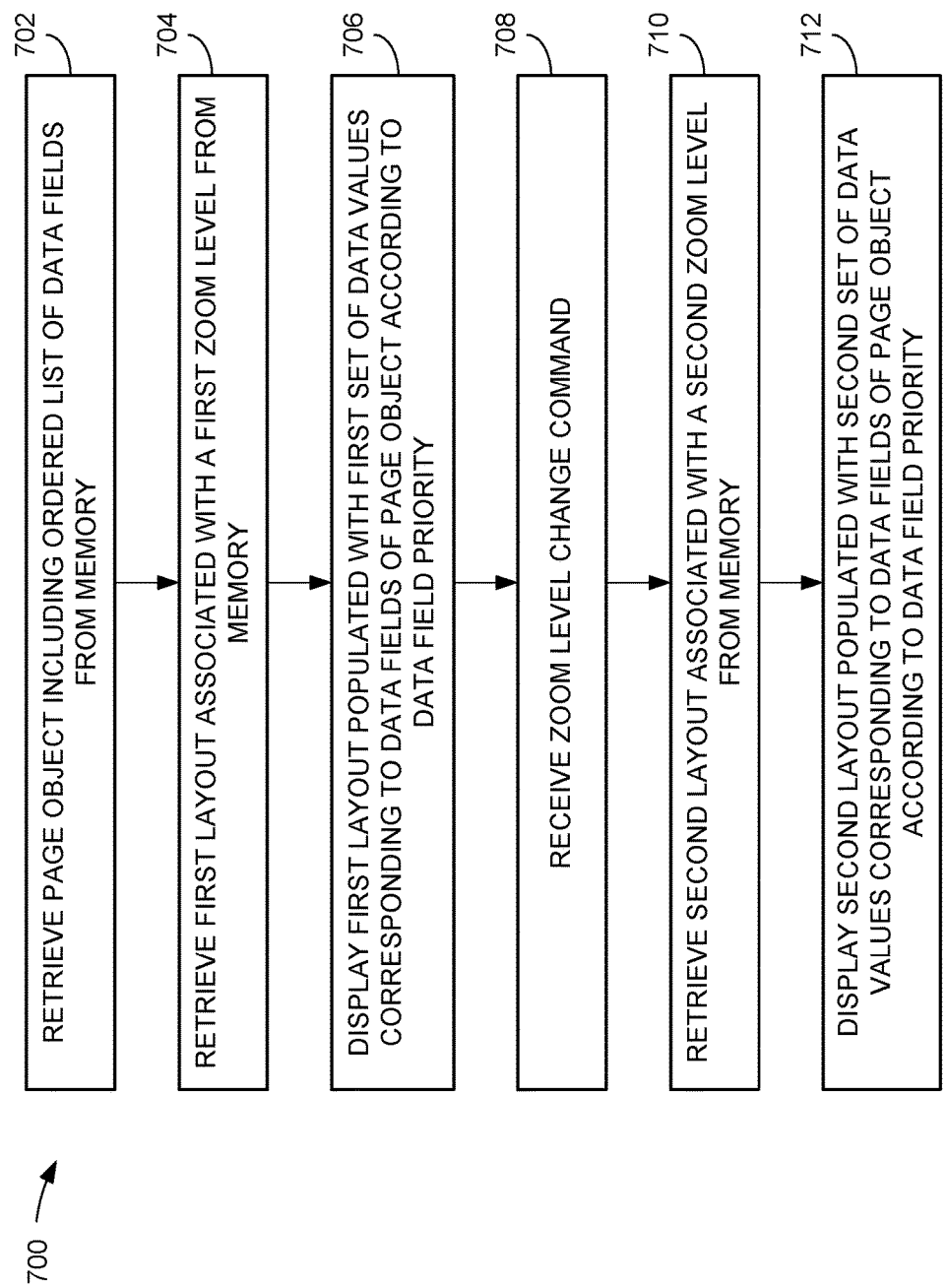
FIG. 7 is a flowchart illustrating a method for displaying exercise data using an exercise computer.

FIG. 7 is flow chart illustrating a method 700 for displaying data on a display of an exercise computer, such as exercise computer 100 of FIGS. 1 and 2. In a first operation 702, a page object, such as the page object 400 of FIG. 4, is retrieved from memory 206 of the exercise computer 100. As previously discussed, the page object 400 generally includes an ordered list 402 of one or more data fields, each of which is associated with a data value also stored in the memory 206. In a second operation 704, a first layout corresponding to a first zoom level is retrieved from the memory 206. For example and as shown in FIG. 4, in certain implementations the page object 400 retrieved during operation 702 includes a current zoom level field 404 in addition to the ordered list 402 and the layout retrieved during the second operation 704 is a layout corresponding to the current zoom level. The first layout generally defines one or more cells for displaying the data values of the ordered list 402. In certain implementations, the one or more cells are assigned a value, rank, or priority corresponding to the rank or priority of a corresponding data field in the ordered list 402. After retrieving the page object and first layout, a first set of the data values are displayed on the display according to the arrangement of the first layout (operation 706). More specifically, the cells of the first layout are drawn on the display and populated with the data values of the corresponding data fields of the page object as determined by the rank/priority of the data fields and the rank/priority of the cells of the first layout. In certain implementations, additional text, such as a title or label for the data field, may also be drawn in each cell or a sub-cell of each cell.

In a subsequent operation 708, a zoom level change command is received by the exercise computer 100 and, more particularly, the processing unit 202 of the exercise computer. In certain implementations, the zoom level change command is generated when a user actuates one of a zoom-in button 114 and a zoom-out button 116. In response to receiving the zoom level change command, a second layout associated with a second zoom level based on the zoom level change command is retrieved from memory (operation 710). The second layout generally defines one or more second cells for displaying a second set of the data values of the page object 400 that includes more or fewer data fields than the first set of data values. Similar to the first cells, the second cells are each assigned a value, rank, or priority corresponding to the rank or priority of corresponding data fields in the ordered list 402. After retrieval of the second layout, the second cells are drawn on the display and populated by the second set of data values as determined by the rank/priority of the data fields and the rank/priority of the cells of the first layout (operation 712).

The second layout may be zoomed-in or zoomed-out relative to the first layout. If the second layout corresponds to a zoomed-in view of the first layout, the second layout generally includes fewer data fields (i.e., the second set of data values is a proper subset of the first set of data values) but may display the data fields in larger text. Similarly, if the second layout corresponds to a zoomed-out view of the first layout, the second layout generally includes more data fields (i.e., the second set of data values is a proper superset of the first set of data values) but may display the data fields in smaller text.

Figure 8:
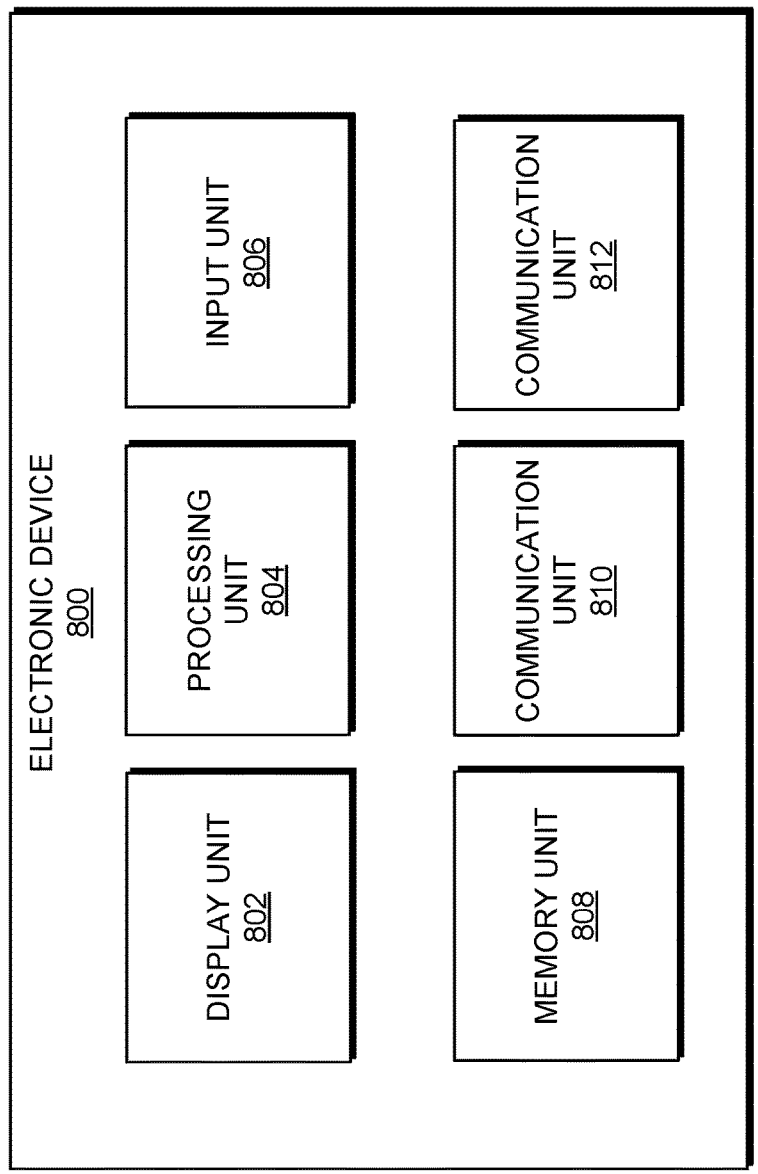
FIG. 8 is an example electronic device that may implement various systems and methods of the presently disclosed technology.

Turning to FIG. 8, an electronic device 800 including operational units 802-812 arranged to perform various operations of the presently disclosed technology is shown. The operational units of the device 800 may be implemented by hardware or a combination of hardware and software to carry out the principles of the present disclosure. It will be understood by persons of skill in the art that the operational units described in FIG. 8 may be combined or separated into sub-blocks to implement the principles of the present disclosure. Therefore, the description herein supports any possible combination or separation or further definition of the operational units. The device may be an exercise computer running the exercise application, or may be a smartphone running the companion application, as possible examples.

In one implementation, the electronic device 800 includes a display unit 802 configured to display information, such as a processing unit 804 in communication with the display unit 802 and an input unit 806, which may be configured to receive input from buttons or sensors communicably coupled to the input unit 806. Various operations described herein may be implemented by the processing unit 804 using data received by the input unit 806 to output information for display using the display unit, and information from connected devices by way of one or more communication units 810-812, each of which may be configured to transmit and/or receive information between the electronic device 800 and other devices by way of one or more wired or wireless communication networks using one or more communication protocols.

The electronic device 800 further includes a memory unit 808 in communication with the processing unit. In one implementation, the memory unit 808 stores an operating system and one or more applications, such as the exercise computer application 210 shown in FIG. 2. The memory unit 808 also stores data for use by the electronic device 800. For example, the memory unit 808 stores data pertaining to one or more page objects, such as the page object 400 of FIG. 4, each of which includes an ordered list of data fields. The memory unit 808 also stores one or more layouts corresponding to different zoom levels at which data values corresponding to the data fields of the ordered lists may be displayed. In certain implementations, the memory unit 808 further stores data values received from one the input unit 806 and/or the communication units 810, 812. For example, in certain implementations, the electronic device 800 can be paired with one or more external sensors coupled to one of the input unit 806 and the communication units 810, 812. The memory unit 808 then stores data collected from or derived from data collected by the external sensors.

Figure 9:
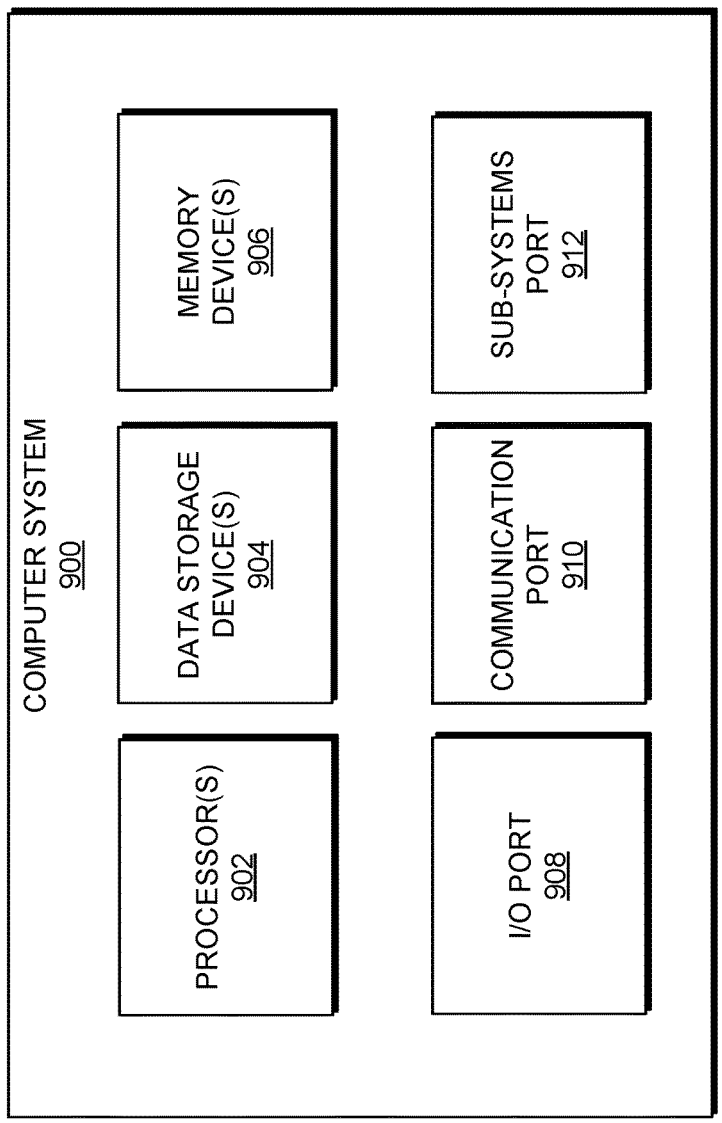
FIG. 9 is an example computing system that may implement various systems and methods of the presently disclosed technology.

Referring to FIG. 9, a detailed description of an example computing system 900 having one or more computing units that may implement various systems and methods discussed herein is provided. The computing system 900 may be applicable to the exercise computer or the remote computer and other computing or network devices. It will be appreciated that specific implementations of these devices may be of differing possible specific computing architectures not all of which are specifically discussed herein but will be understood by those of ordinary skill in the art.

The computer system 900 may be a computing system capable of executing a computer program product to execute a computer process. Data and program files may be input to the computer system 900, which reads the files and executes the programs therein. Some of the elements of the computer system 900 are shown in FIG. 9, including one or more hardware processors 902, one or more data storage devices 904, one or more memory devices 908, and/or one or more ports 908, 910, and 912. Additionally, other elements that will be recognized by those skilled in the art may be included in the computing system 900 but are not explicitly depicted in FIG. 9 or discussed further herein. Various elements of the computer system 900 may communicate with one another by way of one or more communication buses, point-to-point communication paths, or other communication means not explicitly depicted in FIG. 9.

The processor 902 may include, for example, a central processing unit (CPU), a microprocessor, a microcontroller, a digital signal processor (DSP), and/or one or more internal levels of cache. There may be one or more processors 902, such that the processor 902 comprises a single central-processing unit, or a plurality of processing units capable of executing instructions and performing operations in parallel with each other, commonly referred to as a parallel processing environment.

The presently described technology is optionally implemented in software stored on the data stored device(s) 904, stored on the memory device(s) 906, and/or communicated via one or more of the ports 908, 910, and 912, thereby transforming the computer system 900 in FIG. 9 to a special purpose machine for implementing the operations described herein. Examples of the computer system 900 include smartphone type devices and architecture, personal computers, mobile phones, tablets, laptops, personal computers, and the like.

The one or more data storage devices 904 may include any non-volatile data storage device capable of storing data generated or employed within the computing system 900, such as computer executable instructions for performing a computer process, which may include instructions of both application programs and an operating system (OS) that manages the various components of the computing system 900. The data storage devices 904 may include, without limitation, magnetic disk drives, optical disk drives, solid state drives (SSDs), flash drives, and the like. The data storage devices 904 may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 906 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in the data storage devices 904 and/or the memory devices 906, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computer system 900 includes one or more ports, such as an input/output (I/O) port 908, a communication port 910, and a sub-systems port 912, for communicating with other computing, network, or vehicle devices. It will be appreciated that the ports 908, 910, and 912 may be combined or separate and that more or fewer ports may be included in the computer system 900.

The I/O port 908 may be connected to an I/O device, or other device, by which information is input to or output from the computing system 900. Such I/O devices may include, without limitation, one or more input devices, output devices, and/or environment transducer devices.

In one implementation, the input devices convert a human-generated signal, such as, human voice, physical movement, physical touch or pressure, and/or the like, into electrical signals as input data into the computing system 900 via the I/O port 908. Similarly, the output devices may convert electrical signals received from computing system 900 via the I/O port 908 into signals that may be sensed as output by a human, such as sound, light, and/or touch. The input device may be an alphanumeric input device, including alphanumeric and other keys for communicating information and/or command selections to the processor 902 via the I/O port 908. The input device may be another type of user input device including, but not limited to: direction and selection control devices, such as a mouse, a trackball, push-buttons, cursor direction keys, a joystick, and/or a wheel; one or more sensors, such as a camera, a microphone, a positional sensor, an orientation sensor, a gravitational sensor, an inertial sensor, and/or an accelerometer; and/or a touch-sensitive display screen ("touchscreen"). The output devices may include, without limitation, a display, a touchscreen, a speaker, a tactile and/or haptic output device, and/or the like. In some implementations, the input device and the output device may be the same device, for example, in the case of a touchscreen.

The environment transducer devices convert one form of energy or signal into another for input into or output from the computing system 900 via the I/O port 908. For example, an electrical signal generated within the computing system 900 may be converted to another type of signal, and/or vice-versa. In one implementation, the environment transducer devices sense characteristics or aspects of an environment local to or remote from the computing device 900, such as, light, sound, temperature, pressure, magnetic field, electric field, chemical properties, power or torque, physical movement, orientation, acceleration, gravity, heart rate and/or the like. Further, the environment transducer devices may generate signals to impose some effect on the environment either local to or remote from the example computing device 900, such as, physical movement of some object (e.g., a mechanical actuator), heating or cooling of a substance, adding a chemical substance, and/or the like.

In one implementation, a communication port 910 is connected to a network by way of which the computer system 900 may receive network data useful in executing the methods and systems set out herein as well as transmitting information and network configuration changes determined thereby. Stated differently, the communication port 910 connects the computer system 900 to one or more communication interface devices configured to transmit and/or receive information between the computing system 900 and other devices by way of one or more wired or wireless communication networks or connections. Examples of such networks or connections include, without limitation, Universal Serial Bus (USB), Ethernet, Wi-Fi, Bluetooth®, Near Field Communication (NFC), Long-Term Evolution (LTE), and so on. One or more such communication interface devices may be utilized via the communication port 910 to communicate one or more other machines, either directly over a point-to-point communication path, over a wide area network (WAN) (e.g., the Internet), over a local area network (LAN), over a cellular (e.g., third generation (3G) or fourth generation (4G)) network, or over another communication means. Further, the communication port 910 may communicate with an antenna for electromagnetic signal transmission and/or reception. In some examples, an antenna may be employed to receive Global Positioning System (GPS) data to facilitate determination of a location of a machine, vehicle, or another device.

The system set forth in FIG. 9 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium, optical storage medium; magneto-optical storage medium, read only memory (ROM); random access memory (RAM); erasable programmable memory (e.g., EPROM and EEPROM); flash memory; or other types of medium suitable for storing electronic instructions.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. An exercise computer comprising:
  a processing unit in communication with a non-transitory storage and a display;
  a page object stored in the non-transitory storage, the page object comprising an ordered list of data fields, each data field of the ordered list of data fields assigned a respective priority;
  a first page layout stored in the non-transitory storage, the first page layout having a first arrangement of cells for displaying data values for a respective first set of the ordered list of data fields, the first set including a highest priority data field of the ordered list of data fields and a first lower priority data field of the ordered list of data fields;
  a second page layout stored in the non-transitory storage, the second page layout having a second arrangement of cells for displaying data values for a respective second set of the ordered list of data fields, the second set being including the highest priority data field of the ordered list of data fields and a second lower priority data field of the ordered list of data field, the second lower priority data field being different than the first lower priority data field;

wherein the processing unit is configured to:
render the page object on the display according to the first page layout; and
in response to receiving a command to change page layouts, re-render the page object on the display according to the second page layout such that re-rendering the page object according to the second page layout displays at least one more data field or displays at least one less data field as compared to the first page layout.

2. The exercise computer of claim 1 further comprising a zoom button in communication with the processing unit, wherein the command to change layouts is received in response to activation of the zoom button by the user.

3. The exercise computer of claim 1, further comprising:
a housing, wherein each of the processing unit and the display is contained within the housing, the housing including a first edge;
a zoom-in button communicatively coupled to the processing unit and disposed on the first edge; and
a zoom-out button communicatively coupled to the processing unit and disposed on the first edge adjacent to the zoom-in button,
wherein, when actuated by the user, each of the zoom-in button and the zoom-out button is configured to generate a respective command to change page layouts.

4. The exercise computer of claim 1 further comprising a communication unit coupled to the processing unit, wherein the communication unit is configured to communicably couple the exercise computer to a remote computing device and to receive update messages from the remote computing device.

5. The exercise computer of claim 4, wherein the processing unit is further configured to, in response to receiving an update message from the remote computing device, update the ordered list of data fields by at least one of adding a data field to the ordered list of data fields, deleting a data field from the ordered list of data fields, reordering the ordered list of data fields, and changing a data field type of a data field of the ordered list of data fields.

6. The exercise computer of claim 1, wherein the page object is a first page object and the ordered list of data fields is a first ordered list of data fields, the exercise computer further comprising:
a second page object stored in the non-transitory storage, the second page object comprising a second ordered list of data fields,
wherein the processing unit is further configured to, in response to the processing unit receiving a page change command, render the second page object on the display according to a current page layout.

7. The exercise device of claim 1, wherein:
the command to change page layouts is a zoom in command,
the second lower priority data field is of a higher priority than the first lower priority data field, and
re-rendering the page object according to the second page layout displays at least one less data field as compared to the first page layout.

8. The exercise device of claim 1, wherein:
the command to change page layouts is a zoom out command,
the second lower priority data field is of a lower priority than the first lower priority data field, and
re-rendering the page object according to the second page layout displays at least one more data field as compared to the first page layout.

9. A method of displaying exercise data on an exercise computer, the exercise computer including a processing unit coupled to a non-transitory storage and a display, the method comprising:
retrieving a page object from the non-transitory storage, the page object including an ordered list of data fields;
retrieving a first page layout of a plurality of page layouts stored in the non-transitory storage, the first page layout including a first arrangement of cells for displaying a first set of the data fields on the display;
rendering the page object on the display according to the first page layout;
receiving a zoom level change command at the processing unit;
retrieving a second page layout of the plurality of page layouts, the second page layout including a second arrangement of cells for displaying a second set of the ordered list of data fields on the display, wherein the second set of the ordered list of data fields is one of a proper subset of the first set of data fields eliminating at least one data field from the first set of data fields based on the ordering of the list than the first set of data fields or a proper superset of the first set of the data fields adding at least one more data field based on the ordering of the list than the first set of data fields; and
in response to the zoom level change command, rendering the page object according to the second page layout.

10. The method of claim 9, wherein the zoom level change command is a zoom-out command and the second set of the data fields is a proper superset of the first set of the data fields.

11. The method of claim 9, wherein the zoom level change command is a zoom-in command and the second set of the data fields is a proper subset of the first set of the data fields.

12. The method of claim 9, further comprising:
receiving an ordered list update at the processing unit;
modifying the ordered list of data fields based on the ordered list update, wherein modifying the ordered list of data fields includes at least one of adding a data field to the ordered list of data fields, deleting a data field from the ordered list of data fields, reordering the ordered list of data fields, and changing a data field type of a data field of the ordered list of data fields.

13. The method of claim 12, wherein receiving the ordered list update comprises receiving an update message from a remote computing device.

14. The method of claim 9, further comprising:
receiving a page change command at the processing unit;
retrieving a second page object stored in the non-transitory storage, the second page object including a second ordered list of data fields; and
rendering the second page object on the display according to a current page layout.

15. The method of claim 9, wherein each data field is associated with text data stored in the non-transitory storage and rendering the page object according to each of the first layout and second layout further comprises displaying the text data associated with the first set of data fields and the second set of data fields, respectively.

16. The method of claim 9, further comprising:
communicably coupling the exercise computer with a remote computing device; and transmitting exercise computer data pertaining to at least one of the page object, the first layout, and the second layout to the remote computing device.

17. The method of claim 9, further comprising:
communicably coupling the exercise computer with an external sensor;
receiving sensor data from the external sensor, the sensor data pertaining to a data field of the ordered list of data fields; and
storing the received sensor data in a memory location associated with the data field.

18. The method of claim 17, wherein the external sensor includes one of a heart rate monitor, a power meter, a cadence sensor, a speedometer, a gravitational sensor, a positional sensor, an orientation sensor, an inertial sensor, and an accelerometer.

19. The method of claim 9, wherein:
the first set of the ordered list of data fields and the second set of the ordered list of data fields share a common data field,
the first arrangement of cells includes a first cell for displaying the common data field,
the second arrangement of cells includes a second cell for displaying the common data field, and
the second cell has a different size than the first cell such that rendering the page layout object according to the second page layout changes a display size of the common data field.

20. An exercise computer comprising:
a processing unit in communication with a non-transitory storage and a display;
a page object stored in the non-transitory storage, the page object comprising an ordered list of data fields;
a plurality of page layouts stored in the non-transitory storage of the plurality of layouts including a respective arrangement of cells for displaying data values for a respective range of the ordered list of data fields on the display; and
a zoom button in communication with the processing unit, wherein the processing unit is configured to:
render the page object on the display according to a first page layout of the plurality of page layouts, the first page layout having a first arrangement of cells corresponding to a first range of the ordered list of data fields; and
in response to receiving a command to change page layouts, the command received in response to activation of the zoom button, re-render the page object on the display according to a second page layout of the plurality of page layouts, the second page layout having a second arrangement of cells corresponding to a second range of the ordered list of data fields,
wherein:
the zoom button is a zoom-in button,
the second range is less than the first range such that re-rendering the page object according to the second page layout displays fewer data fields than rendering the page object according to the first page layout, and
each of the first range and the second range includes a common data field of the ordered list of data fields, the cell of the second arrangement for displaying the common data field being larger than the cell of the first arrangement for displaying the common data field.

21. An exercise computer comprising:
a processing unit in communication with a non-transitory storage and a display;
a page object stored in the non-transitory storage, the page object comprising an ordered list of data fields;
a plurality of page layouts stored in the non-transitory storage of the plurality of layouts including a respective arrangement of cells for displaying data values for a respective range of the ordered list of data fields on the display; and
a zoom button in communication with the processing unit, wherein the processing unit is configured to:
render the page object on the display according to a first page layout of the plurality of page layouts, the first page layout having a first arrangement of cells corresponding to a first range of the ordered list of data fields; and
in response to receiving a command to change page layouts, the command received in response to activation of the zoom button, re-render the page object on the display according to a second page layout of the plurality of page layouts, the second page layout having a second arrangement of cells corresponding to a second range of the ordered list of data fields,
wherein:
the zoom button is a zoom-out button,
the second range is greater than the first range such that re-rendering the page object according to the second page layout displays more data fields than rendering the page object according to the first page layout, and
each of the first range and the second range includes a common data field of the ordered list of data fields, the cell of the second arrangement for displaying the common data field being smaller than the cell of the first arrangement for displaying the common data field.

22. A non-transitory tangible computer-readable storage media storing computer-executable instructions for performing a computer process on an exercise computer, the exercise computer including a processing unit in communication with one or more memory devices and a display, the computer process comprising:
retrieving a page object from the one or more memory devices, the page object including an ordered list of data fields;
retrieving a first page layout from the one or more memory devices, the first page layout including a first arrangement of cells for displaying a first set of the data fields on the display;
rendering the page object on the display according to the first page layout;
receiving a zoom level change command;
retrieving a second page layout from the one or more memory devices, the second page layout including a second arrangement of cells for displaying a second set of the ordered list of data fields on the display, wherein the second set of the ordered list of data fields is one of a proper subset of the first set of data fields eliminating at least one data field than the first set of data fields based on the ordering of the ordered list or a proper superset of the first set of the data fields adding at least one more data field than the first set of data fields based on the ordering of the ordered list; and
rendering, in response to receiving the zoom level change command, the page object according to the second layout.

23. An exercise computer comprising:
a housing;
a display disposed within the housing, the display configured to selectively display each of a plurality of layouts for presenting data values pertaining to ranked data fields, each of the plurality of layouts corresponding to a different zoom level wherein each zoom level includes a different quantity of data values pertaining to the ranked data fields;

a zoom-in button disposed on the housing and in communication with the display, wherein in response to actuation of the zoom-in button, the display changes to a first layout in which fewer data values are displayed relative to a current layout; and a zoom-out button disposed on the housing and in communication with the display, wherein in response to actuation of the zoom-out button, the display changes to a second layout in which more data values are displayed relative to the current layout.

24. The exercise computer of claim 23 wherein:

the housing includes a sidewall, and the zoom-in button and the zoom-out button are adjacent each other and extend through the sidewall.

* * * * *